United States Patent
Robinson et al.

(10) Patent No.: US 6,568,419 B1
(45) Date of Patent: May 27, 2003

(54) DISPOSABLE FLUID CONTROL ISLAND

(75) Inventors: Allan Robinson, Minneapolis, MN (US); Dennis Ristvedt, Burnsville, MN (US)

(73) Assignee: Promethean Medical Technologies, Inc., St. Paul, MN (US)

( * ) Notice: Subject to any disclaimer, the term of this patent is extended or adjusted under 35 U.S.C. 154(b) by 0 days.

(21) Appl. No.: 09/020,708

(22) Filed: Feb. 9, 1998

(51) Int. Cl.[7] .............................. A61M 1/00; F16L 55/07
(52) U.S. Cl. ........................... 137/312; 50/606; 50/952; 604/356; 137/1; 137/565.01; 137/362; 141/86; 141/98; 220/571
(58) Field of Search ...................... 137/1, 312, 362, 137/561 R, 565.01; 5/420, 484, 487, 606, 952; 141/86, 98; 184/106; 220/571, 573; 238/1; 180/69.1; 296/38; 269/15; 604/356

(56) References Cited

U.S. PATENT DOCUMENTS

| | | | | |
|---|---|---|---|---|
| 2,851,311 A | * | 9/1958 | Gibbs | 182/222 |
| 4,243,214 A | * | 1/1981 | Larooka | 5/606 |
| 4,295,235 A | * | 10/1981 | Deitz | 5/473 |
| 4,679,590 A | * | 7/1987 | Hergenroeder | 137/312 |
| 4,718,653 A | * | 1/1988 | Rothman | 5/606 |
| 4,729,404 A | * | 3/1988 | Hergenroeder | 137/312 |
| 4,811,937 A | * | 3/1989 | Rothman | 5/606 |
| 4,870,710 A | * | 10/1989 | Hartmann | 5/484 |
| 5,189,743 A | * | 3/1993 | Difloe | 5/461 |
| 5,199,457 A | * | 4/1993 | Miller | 137/312 |
| 5,492,158 A | * | 2/1996 | Haag | 137/312 |
| 5,547,312 A | * | 8/1996 | Schmitz, Jr. | 137/312 |
| 5,738,139 A | * | 4/1998 | Dechard | 137/312 |
| 5,775,869 A | * | 7/1998 | Bishop | 137/312 |

* cited by examiner

Primary Examiner—George L. Walton
(74) Attorney, Agent, or Firm—Schwegman, Lundberg, Woessner & Kluth, P.A..

(57) ABSTRACT

A disposable fluid control island for workers is made of a broad, shallow tray or flat open-topped container that is filled with a stiff mesh, grid, grille or net upon which workers may stand. Water, oil, blood and other liquids pass through the mesh easily and are retained in the tray. Workers are supported above the accumulated liquids by the support medium. The apparatus helps to keep the feet of workers dry, reduces the likelihood of slipping, and prevents liquids from dispersing. The disposable fluid control island is particularly well-suited for use during orthopedic surgical procedures, but can be used with other activities including plumbing repairs, handling of hazardous materials, and other medical procedures. Fluid collected by the disposable fluid control island may be removed by vacuum or liquid drains, sealed into containers, and disposed of appropriately given the nature of the materials. The fluid control island may then be sealed within a bio-hazard bag or other appropriate containment for disposal. The edges of the container may be sloped to provide a transition between the surrounding floor and the support medium. In an alternate version, the support mesh and tray may be fitted within a permanent receiving station or recessed portion of the floor.

27 Claims, 9 Drawing Sheets

DISPOSABLE FLUID CONTROL ISLAND

TECHNICAL FIELD

The present invention relates to methods and apparatus for control of fluids on work area floors. More specifically, the invention relates to methods and disposable apparatus for keeping the footgear and the feet of workers out of fluids that fall to the floor in a work area. In particular, the present invention provides a macro-porous surface upon which workers may stand and through which fluids may easily pass to be collected in a fluid collection vessel underlying the porous material.

BACKGROUND AND SUMMARY

A problem affecting the health and safety of a variety of workers is that of providing a safe, non-slippery, dry area upon which the workers can stand. Hospital operating room personnel are routinely required to stand and work in conditions in which the floor is inundated with several liters of blood, bodily fluids, and saline solution during a single procedure. Drilling, sawing, and other metalworking operations may wet floors with lubricants, coolants, or other liquids and make the nearby floors difficult, unpleasant, or dangerous places to work. Many die casters, chemists, machinists, maintenance workers, and workers in other occupations encounter floor surfaces that are wetted either frequently or periodically any of a substantial variety of release agents, aqueous solutions, cleaning formulations, reagents, waste, spillage, and the like.

Various types of grating structures that support workers above locations where, liquid or fluid, accumulates, or collects, may be fitted on flooring that is routinely wet. Even if puddles do not develop on a work surface floor, a small amount of liquid is frequently enough to make a floor slippery. Floor drains may be required to keep some floors free of puddles. Some other situations, can be improved easily by applying anti-skid materials to the floor. In other instances, a roughened finish may be applied to cast-in-place floor surfaces such as concrete. In some work environments, those remedies may be impractical.

For example, the appearance of some flooring materials can be permanently damaged by spills of materials such as paints, rust, water, or solvents that may be transported or used nearby. A plumber may be required to repair or replace appliances and component lines at locations where expensive carpets are installed. Trays, towels, pans, and drop cloths are often used to protect existing floor covering material on an ad hoc basis, often with a less than desirable outcome because the activity may occur seldom, if ever, at any particular location. Many tradespeople do not routinely provide satisfactory mats or other equipment to catch spills and prevent damage to floors during routine maintenance or in response to needed repairs. Some liquid materials that fall to the floor cannot be safely drained through ordinary floor drains because the materials are chemicals that pose environmental hazards. Other materials that fall to the floor in certain work places can present bio-hazards.

Even in facilities where the floors are routinely wetted, specific conditions can make the use of gratings difficult or impossible. In food handling operations, it may be impossible to clean grating-covered floors with sufficient thoroughness to prevent potential contamination of the product. Likewise, it may be impossible to clean grating surfaces sufficiently frequently and with sufficient thoroughness to prevent contamination and infection of other people, especially those who must work in damp conditions such as those found in hospital operating theaters. It may be necessary to recover the potentially harmful spillage and waste from such workplaces for subsequent treatment, recovery, measurement, incineration, re-processing, or disposal in accordance with applicable laws, policies, and regulations.

Persons skilled in the art of operating room design and in hospital sanitation have long sought ways to reduce the problems caused by the liquid materials that inundate floors in operating rooms and emergency rooms. Although several attempts at creating improved work areas have been made, none has produced a system that is both practical to use and practical to sterilize.

In U.S. Pat. No. 4,635,913, issued Jan. 13, 1987; U.S. Pat. No. 4,718,653, issued Jan. 12, 1988; and U.S. Pat. No. 4,811,937, issued Mar. 14, 1989, Rothman disclosed a series of Portable Surgical Drainage Platforms. The inventions he developed could assist surgeons and other surgical staff by supporting the personnel on grating and removing liquid that falls through the grating. The platforms are, however, rather heavy and are also difficult to sterilize at all, especially in the short amount of time that may available between surgeries.

LaRooka received U.S. Pat. No. 4,243,214 on Jan. 6, 1981, for her Irrigation-Debridement-Repair Caddy. That disclosure is directed to an apparatus that can be placed under an extremity of a person during a surgical procedure. The Irrigation-Debridement-Repair Caddy is designed to collect some of the irrigation saline solution and excised tissue that would otherwise drip onto the floor and collect the fluid in a closeable bottle for eventual disposal.

Other workers, such as Gibbs in his U.S. Pat. No. 2,851,311, issued Apr. 22, 1955, have developed a variety of ingenious portable scaffolding and grate-retaining devices.

Presently known methods and apparatus have been unable to implement a solution to the various problems encountered by people who work in areas where wet floors are routinely encountered. In hospital operating rooms, for example, the method for controlling wet floor problems is often merely to scatter disposable absorbent blankets, pads, or mats on the floor. Following the surgery, the absorbent material may be weighed to measure the amount of fluid lost by the patient during the procedure. Typical absorbent blankets are made of materials similar to those used to make disposable diapers. It may readily be appreciated that standing, walking, and working with several pieces of that type of material disintegrating on the floor surface is difficult, at best. Unfortunately, those activities are especially difficult under actual conditions because the considerable activity during a surgical procedure tends to bunch up the absorbent materials. Under these circumstances, the potential for tripping or other accidents is further aggravated because the concentration of workers is directed to matters other than the status of the floors on which they stand.

What is needed, then is a disposable fluid control island for selectably collecting, retaining and draining fluids from the vicinity of the feet of workers comprising a generally broad, shallow, impermeable vessel having a generally horizontal, floor-contacting, bottom portion and a generally vertical peripheral portion, a foot-supporting portion disposed within and substantially filling the vessel, the foot-supporting portion having a top surface spaced apart from the vessel bottom portion by filler comprised of; a vertical compression resisting portion having sufficient resistance to compression to support workers standing on the foot-supporting portion, and a liquid retaining portion comprised of fluid-absorbing material, a link formed at the periphery of the vessel for retaining in proximity to one another an assembly comprised of at least one vessel and at least one other component from the group of components consisting of vessels and inclined transitions, the inclined transitions being positionable at the periphery of a vessel assembly and extending between the floor and the top surface of the foot-supporting portion, and means for closing the apparatus for retaining collected fluids until final disposition of the fluid collecting island is effected.

Embodiments of the present disclosure meet these needs, and more, by solving the long-recognized problem of containing and removing fluids from floors in the vicinity of workers. The present disclosure teaches a disposable, fluid containing and draining vessel filled with porous material having substantial void space that supports workers. In a preferred embodiment, the porous supporting material is a stiff, hydrophobic, non-woven, polymer fiber mat that has substantial void space. Many other configurations for the supporting material may be used without departing from the scope of this disclosure, including, without limitation, materials such as coarsely woven rope mats, nibs or bristles that extend vertically from the bottom of the vessel, and any of the number of materials and techniques by which door mats can be made.

The support material preferred, however, is lightweight so that the fluid control island may be shipped, stored, and handled easily by personnel who have no special training, physical abilities or handling equipment. It is also preferred that the support material be inexpensive so that the fluid control island can be disposed of destructively to reduce the potential for environmental and health hazards that might result from attempts to clean and re-use the components. It is also preferred that the support material have good shelf life. Other desirable support material characteristics include: that it is non-slippery when wet, that it remains flat on the floor surface while the fluid control island is in use, that liquids may be readily removed from the support material for recovery or analysis, that it be easily bonded to the vessel material, that it does not cause allergic reactions, that it does not create difficult disposal problems, and that it can be folded or rolled for easy shipping.

The support material is contained within a shallow vessel that prevents fluids that fall onto the support material from contacting the floor. The vessel may be formed in many different configurations, however, it may be most useful when it covers a fairly large area. For example, a fluid control island vessel may be 2½' wide, 4' long, have a depth and mesh thickness of ¾" with a drainage slope of ⅛" over the length and/or the width. The slope causes the liquid to flow toward one end of the vessel making it possible to remove the fluid easily either with a vacuum source and fluid collection canister or with use of a pump capable of pumping the specific liquids that a particular vessel collects. Such a fluid control island vessel, with the support mat in place, can contain several liters of fluids. That surge capacity makes it possible to use a relatively low rate of fluid removal with an inexpensive removal system, whether vacuum operated or pumped directly, yet still have sufficient capacity to collect and remove all the fluids collected in the vessel during a procedure.

The disposable fluid control island may be furnished with transition members that make the change in elevation from the fluid control island to the floor gradual. It can be seen that the transition from the surrounding floor to the fluid controls island support surface is approximately 1¼" which will be easily tolerated by personnel if a transition zone of approximately 6" is provided. It is also to be understood that areas or rooms where the disposable fluid control island is used frequently may be fitted with floor indentations sized to receive the disposable fluid control island vessel with minimal difference in the elevation of the support surface and the surrounding floor.

The support surface-containing vessel may advantageously be fitted into other equipment or structures, whether portable, temporary, fixed, or permanent. For example, a temporary or mobile testing laboratory may benefit from having an area adapted for receiving the support surface-containing vessel. A specialized work area such as a portable surgical set-up for knee-replacement surgery may have fixtures, instruments, tools, supplies and other needed items both available and located at the most appropriate locations to enable surgical personnel to carry out a particular procedure or a particular class of procedures with the utmost speed and efficiency. It would be necessary to transport such a set-up between operating rooms and to move it to and from storage to accommodate a different standardized set-up, such as one for hip replacement surgery or for cardiac by-pass surgery.

The time saving and productivity enhancement potential that may be gained by utilization of such procedures and equipment have not been readily realizable absent the apparatus and methods of the present disclosure. The difficulty of properly cleaning and sterilizing such platforms and the associated gratings and support members between procedures is responsible, at least in part, for the reluctance of decision makers to adopt such systems and set-ups. By fitting the present support surface-containing vessel to such a portable surgical station, it is possible to verify the amount of liquids used and released and to easily dispose of the bio-hazard presenting tissues and fluids by incineration or other approved techniques.

When the area to be protected or the area in which the work will be performed, or carried out, is larger than the size of a single fluid control island member, it is desirable to fit vessel/support material modules together to cover the needed floor area by making a disposable fluid control island of any desired size. The modules may be sized so that interconnection is easy and versatile. Mating edge connections may be provided on the modules so that adjacent modules may be readily linked together. It is also possible to form all edges of the modules identically and then to add a separate connection channel or adaptor. It may also be satisfactory in some instances to use adhesives or adhesive tapes to connect modules. In some applications, linking or connecting adjacent modules may not be necessary. It may be possible to hold the modules in the correct position with relocatable, high tack adhesive tape or pre-applied relocatable high tack adhesives that will prevent the disposable fluid control island modules from shifting after being placed at the desired location on the floor.

One method for preventing wet floors in work areas and for supporting the feet of workers above liquid that falls or otherwise comes into contact with the floor (including the vessel and support material) in an area in which workers work can be comprised of the steps of placing a generally broad, shallow, impermeable vessel having a generally horizontal, floor-contacting, bottom portion and a generally vertical peripheral portion on the floor of the work area, placing a foot-supporting portion that has a bottom surface and a fluid-permeable top surface spaced apart from the bottom surface by filler in the vessel, retaining fluid that falls in the vicinity of the feet of the workers in the vessel, and supporting the feet of workers above liquid that accumulates in the vessel. Additional steps of this method may also include draining the collected liquid from the vessel automatically using a pump. The fluid collection performance may be enhanced by placing an inclined transition portion between the floor and the vessel. This method may readily carried out using the structure disclosed here.

Fluids that reach the fluid control island disclosed herein will normally be caused to flow toward a collection point by sloping the bottom of the vessel. When more than one module is used at a time, it is possible to connect each module drain to a manifold so that a single collection, fluid transport, and receiving container can be used during each procedure. The manifold can be made of the same tubular material that forms hydraulic connections with a multiplicity of fluid-conducting drain tubes or conduits. When the procedure is one that may result in the apparatus intercepting more fluid than a single container holds, additional receiving containers may be connected serially. The vessel side walls may be provided with knock-out plugs or other selectable fluid transmitting devices such as valves, stoppers, cut-outs, or other bulkhead feed-through elements so that the fluids may flow or be drawn into tubing and pumped or vacuum transported from the vessel and ultimately to an appropriate disposal process. It may be desirable to form a series of generally parallel channels that are oriented toward the location of the drain to reduce the amount of fluid retained by the vessel and support surface when the procedure is concluded and it is desired to remove the disposable fluid control island and to then dispose of it.

DETAILED DESCRIPTION OF THE PREFERRED EMBODIMENT

Figure 1:
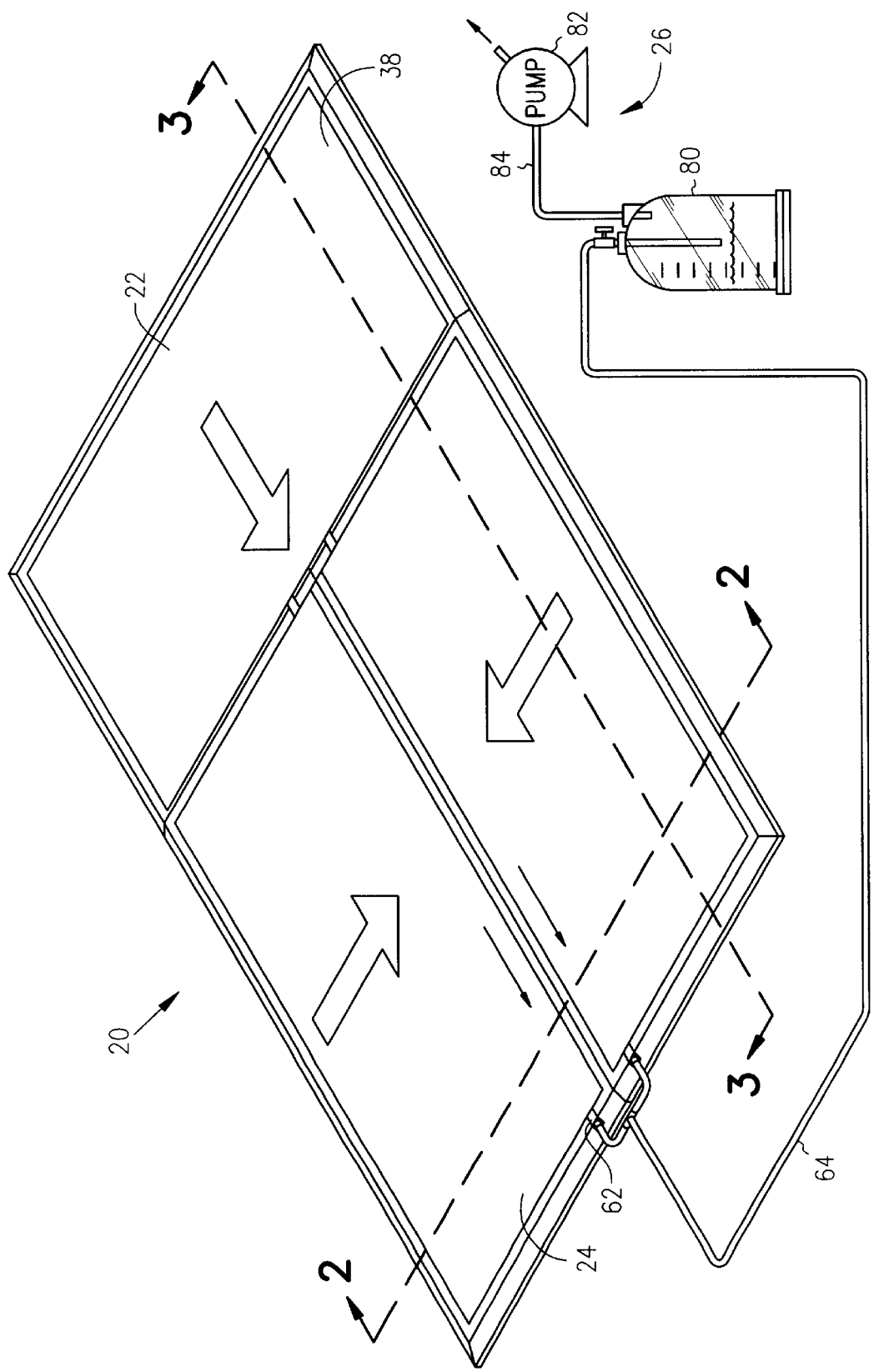
FIG. 1 is a perspective view showing a three-section disposable fluid control island with vacuum operated fluid removal provision.

Viewing first FIG. 1, an overall perspective view of a version of the disposable fluid control island 20 is shown. The version shown in FIG. 1 shows an assembly of three fluid control modules 22 that are interconnected to form an essentially continuous foot-supporting surface 24 upon which personnel may stand as they work. An overall drain system 26 removes fluids that pass through the foot-supporting surface and are collected by a broad, shallow vessel 28.

Figure 2:
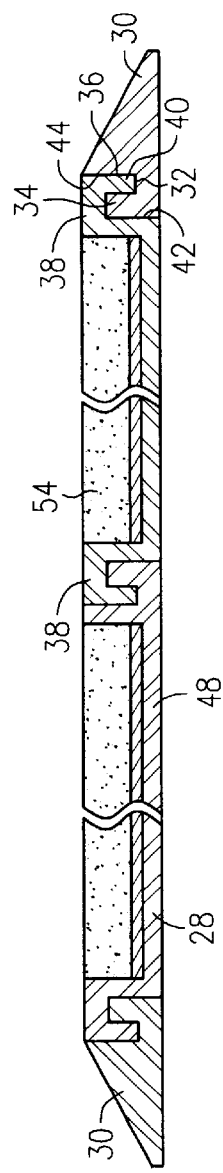
FIG. 2 is a cross-section of the disposable fluid control island of FIG. 1 taken at 2—2.
Figure 3:
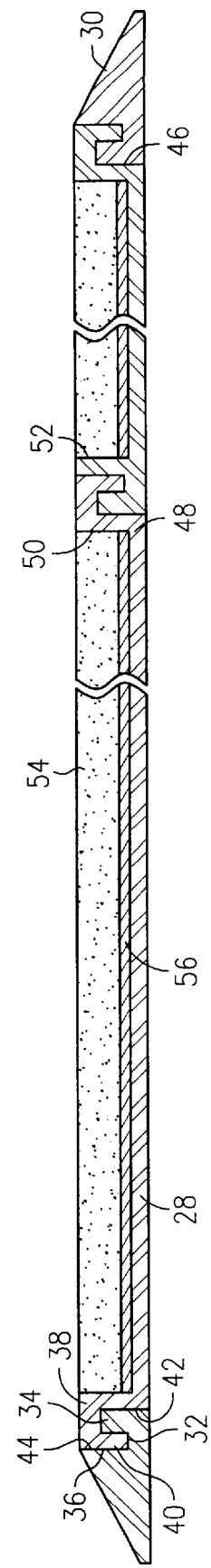
FIG. 3 is a cross-section of the disposable fluid control island of FIG. 1 taken at 3—3.
Figure 4:
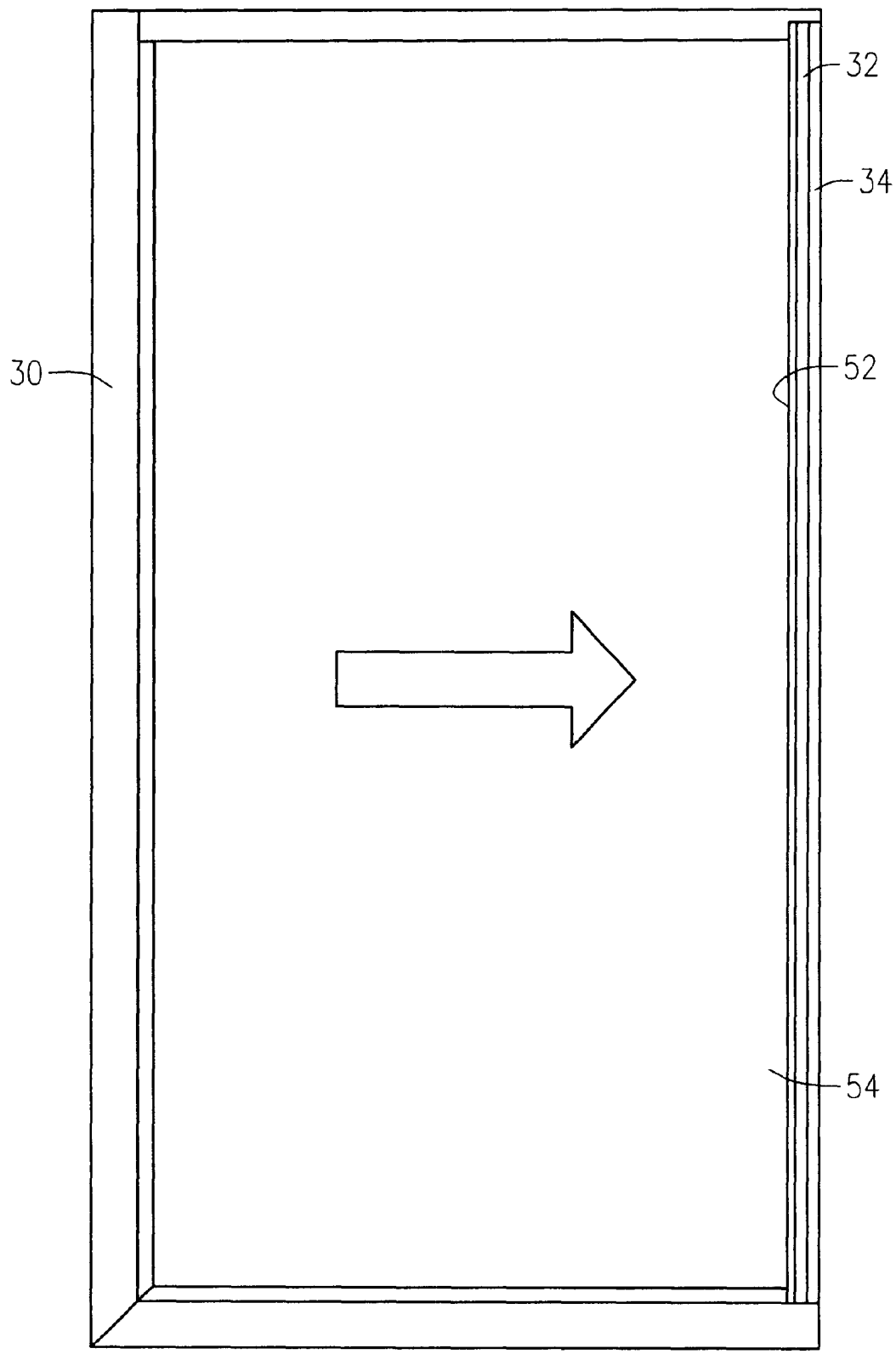
FIG. 4 is a plan view of a first section of the disposable fluid control island of FIG. 1.
Figure 5:
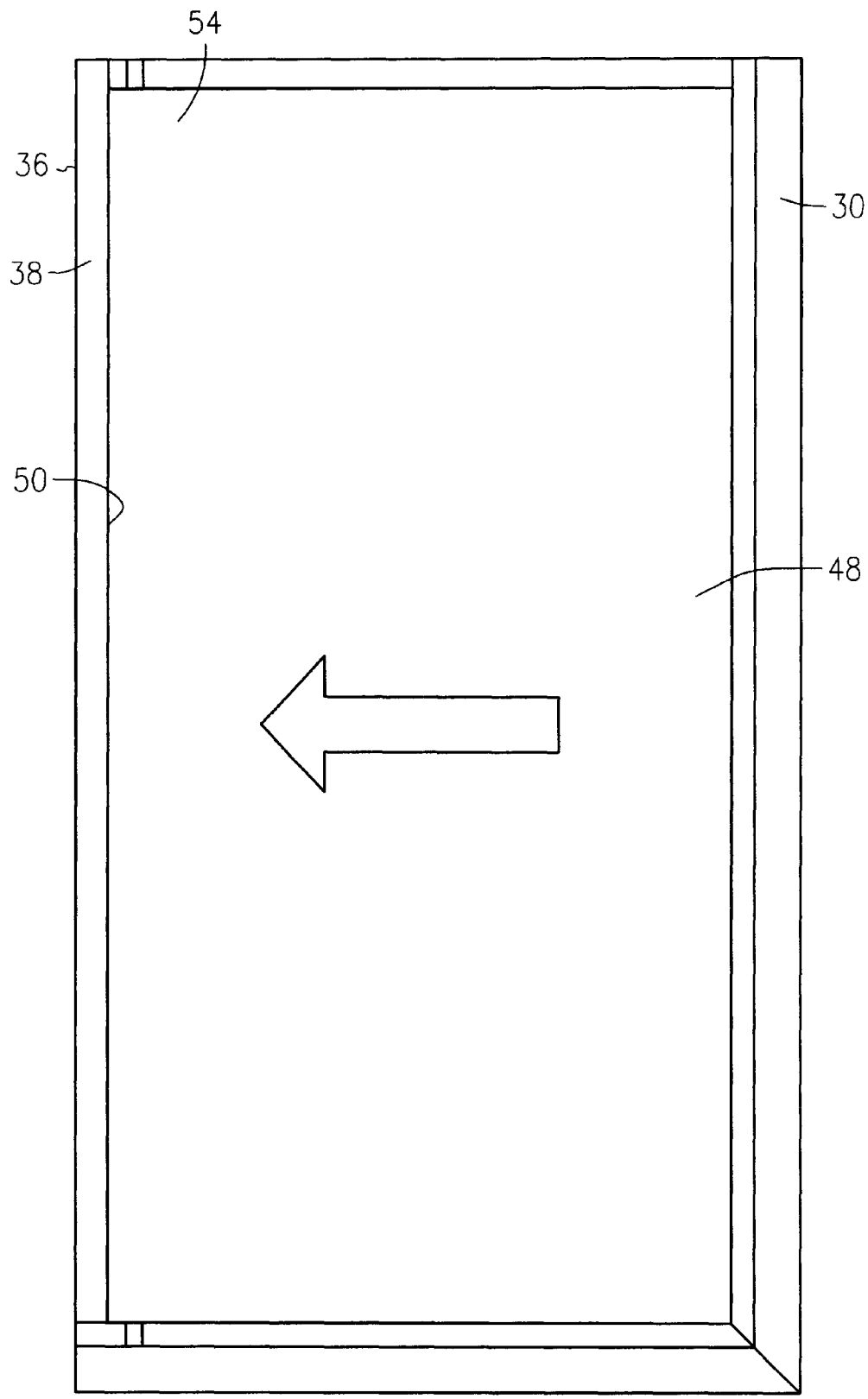
FIG. 5 is a plan view of a second section of the disposable fluid control island of FIG. 1.

The collection vessel 28 may be viewed more readily in FIG. 2 and FIG. 3 which are sections taken at 2—2 and 3—3 of FIG. 1, respectively. A perimeter transition 30 allows personnel to more easily travel between the surrounding floor and the disposable fluid control island 20, especially when it is necessary to situate wheeled equipment there.

The interlocking perimeters of the individual modules 22 can be made in a variety of ways. In the embodiment shown in FIG. 2, FIG. 3, FIG. 4, and FIG. 5, a channel 32 is formed between the lip 34 and the channel wall 36 of the transition 30. An inverted channel, or latch 38, is formed between a latch lip 40 and the latch wall 42. The outermost vertical surface of the latch portion is a latch perimeter wall 44 that fits against the channel wall 36 portion of the transition 30. The transition inner wall 46 is the innermost vertical surface of the transition 30 and fits against the latch wall 42. The interlocking of the channel lip 34 with the latch 38 and the latch lip 40 with the channel 32 prevent the components of the disposable fluid control island from separating during use.

The fluid control island modules 22 may be fabricated with any combination of latches 38 and channels on the perimeter edges so that it will be easy to group modules 22 into larger arrays. It is also possible to finish all perimeter edges of the modules 22 identically with channels 32 and connect the channel lips of adjacent modules 22 with a separate latch strip in the form of a mating inverted "U" that would hold adjacent modules 22 fixedly together during a procedure but could easily be removed for disposal of the modules 22 and such a connecting latch strip.

Both FIG. 2 and FIG. 3 show mating channel 32 and latch 38 sections as they would be used to connect transitions 30 to the modules 22 in addition to interconnecting adjacent modules 22.

The modules 22 can be manufactured in several configurations and sizes. One version of the invention, includes a shallow vessel 48 formed by a floor-contacting polymer sheet, extrusion, or casting peripherally bounded by the inner surface of the vessel latch wall 50 and/or the inner surface of the vessel channel wall 52.

Affixed to the vessel 28 portion of each module is a foot-supporting material 54 which may be a sturdy non-woven mat. Fluids can easily penetrate the surface such a mat which has the additional benefit of reducing splatter and splash when liquids fall to the material 54 which substantially fills the vessel 28.

The upper surface of the bottom of the vessel may have drainage grooves 56 to enhance fluid removal. FIGS. 4–9 show with outline arrows the direction of fluid flow and of the orientation of the drain grooves in the different modules 22 and configurations. In particular, FIGS. 2, 3, and 7 show the slope of the bottom of the vessel 28 to enhance drainage.

Figure 6:
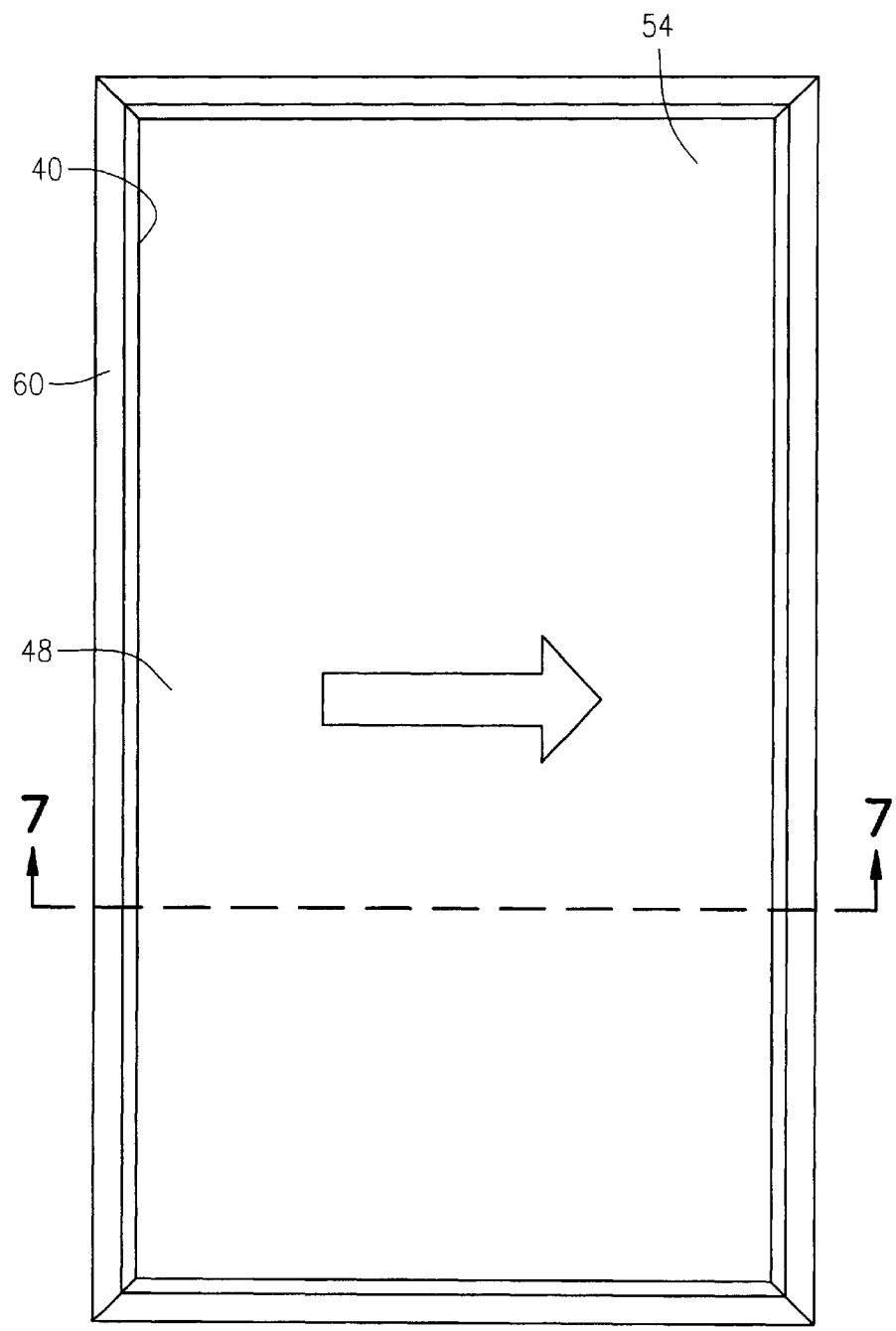
FIG. 6 is a plan view of a single section disposable fluid control island that is similar to the multiple part disposable fluid control island of FIG. 1.
Figure 7:
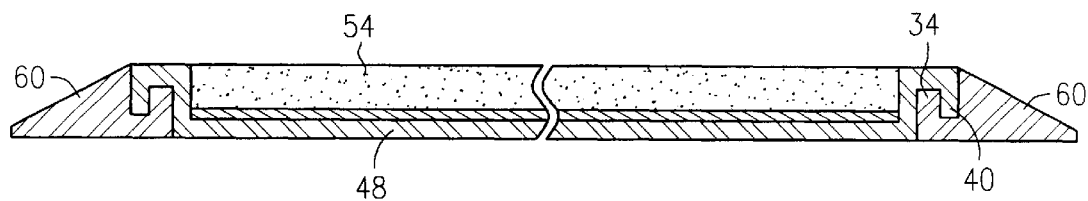
FIG. 7 is a cross-section view of the disposable fluid control island of FIG. 6 taken at 7—7.

In FIG. 6, and FIG. 7, an alternative embodiment of a fluid control island module 22 is depicted. The alternate transition 60 differs from the transition 30 in that the latch lip 40 is molded to the upper surface. As a consequence, the fluid-containing vessel 48 is formed having a channel lip 34 at its periphery that mates with the latch lip 40. The fluid control island module 22 shown in FIG. 6 and FIG. 7 is configured as a stand-alone module which may be well-suited for use during emergency plumbing repairs, hand surgery, or other tasks in which it is not necessary to link several modules 22 together.

It is to be understood that the fluid control island 20 shown in FIG. 6 may also be molded and packaged in a unitary configuration. The transition 60 may be bonded to, or molded integrally with, the vessel 48. Likewise, the foot-supporting material 54 may be permanently affixed to the vessel 48 and/or the transition 60 rather than using a separate latch 38.

Figure 8:
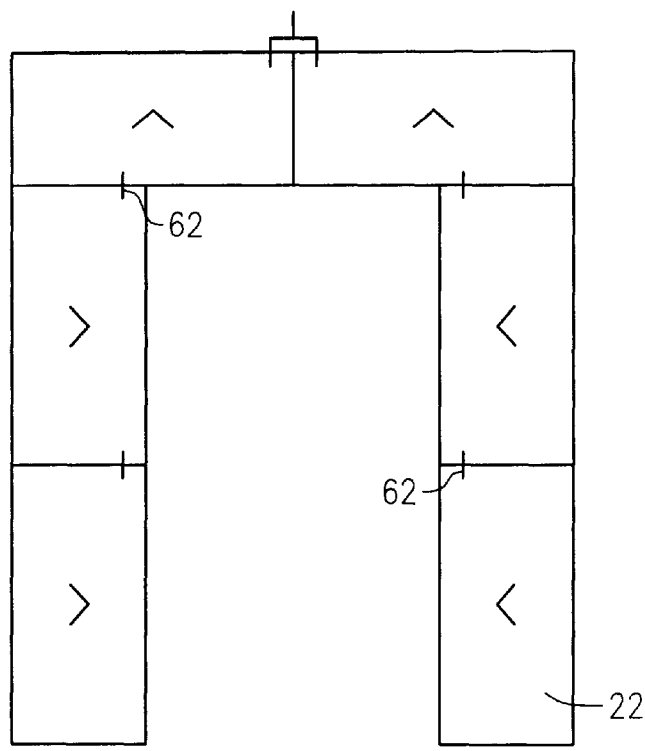
FIG. 8 is a drainage flow plan view of a six-section disposable fluid control island similar to the disposable fluid control island shown in FIG. 1.
Figure 9:
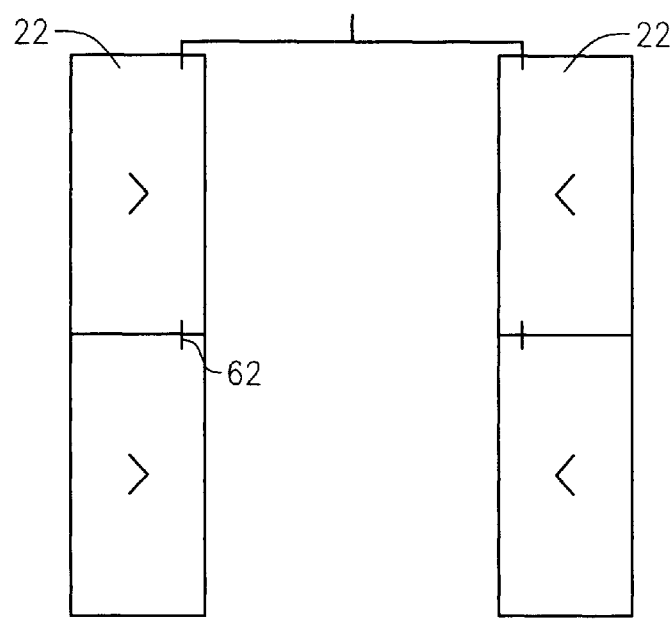
FIG. 9 is a drainage flow plan view of a four-section disposable fluid control island similar to the disposable fluid control island shown in FIG. 1.

FIG. 8 and FIG. 9 show alternative configurations of linked fluid control island module 22 assemblies. Other configurations are expected to be used as equivalents of the representative configurations shown in FIGS. 1–10 and are specifically included as part of this disclosure. Arrows on each module show the direction collected fluids will flow.

Figure 10:
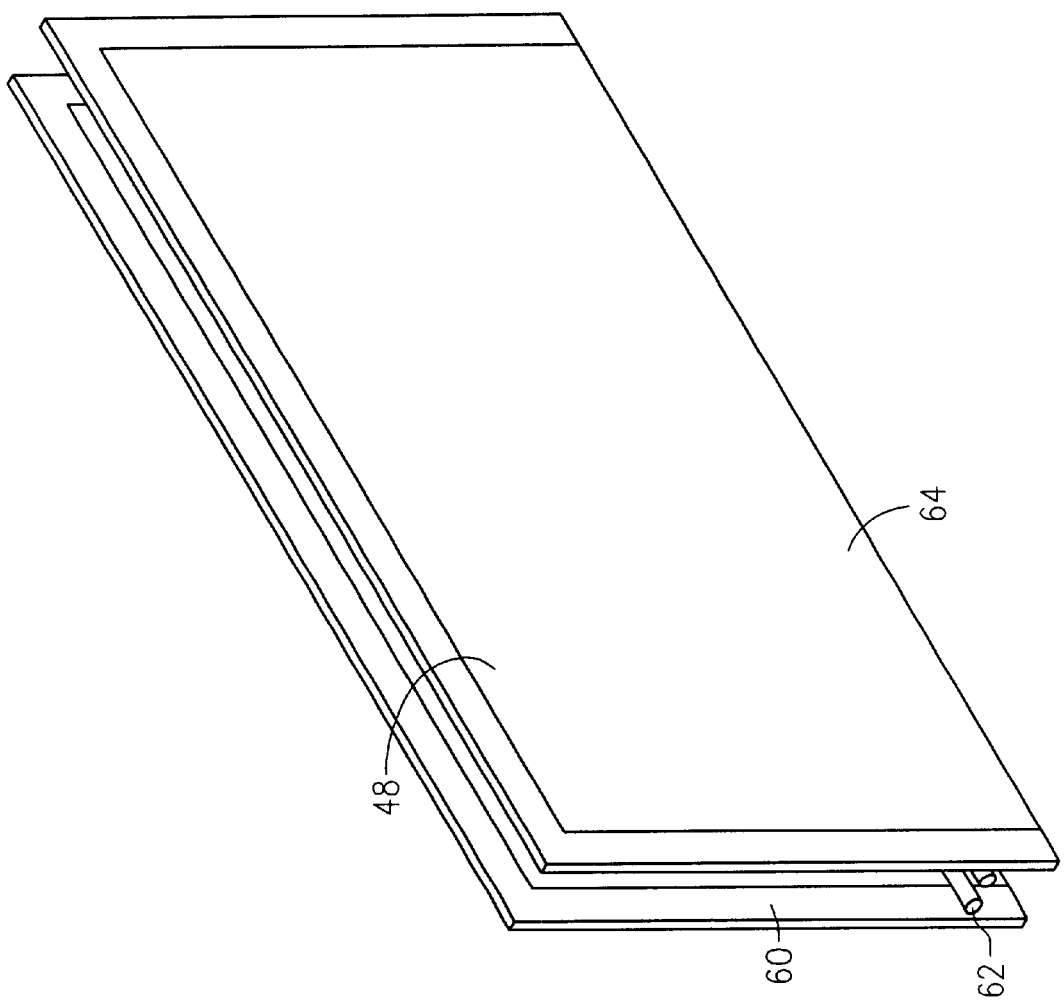
FIG. 10 shows, in a folded configuration, a perspective view of an alternative, foldable embodiment of the disposable fluid control island of FIG. 6.

FIG. 10 depicts another version of the apparatus of this disclosure. Two modules are designed to fold integrally for shipment and for disposal. Drain feed-throughs 62 extending from the central portion of the foldable module 64.

Figure 11:
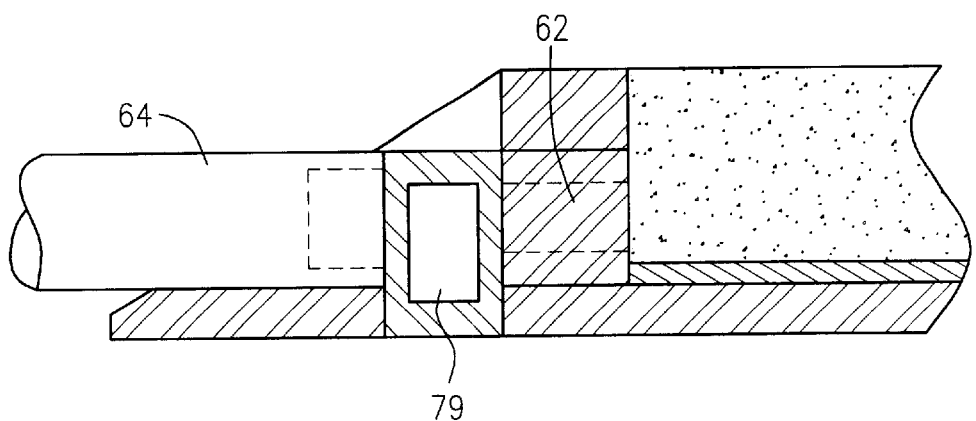
FIG. 11 is a detail of an embodiment of the drain of the disposable fluid control island of FIG. 10.

FIG. 11 shows in greater detail a cross-section of a feed-through 62 that can be used to conduct fluids from one module 22 to another or to drain fluids away from the modules 22 through a drain hose 64 for disposal.

Figure 12:
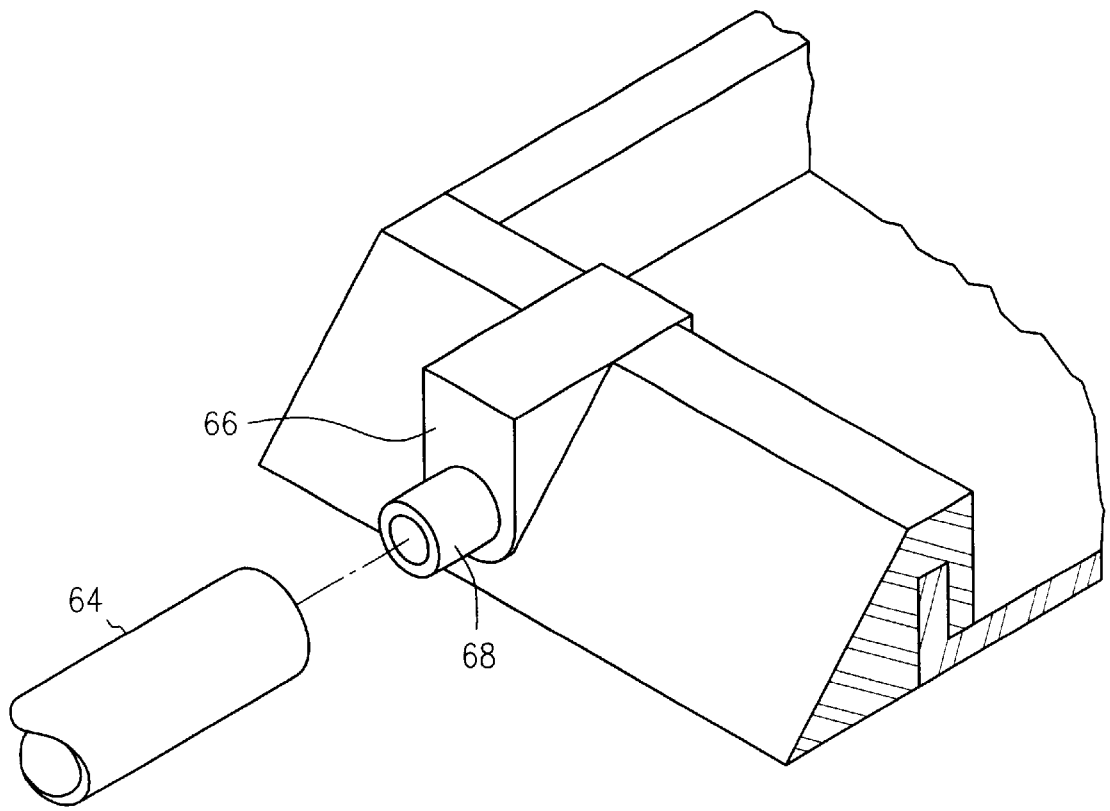
FIG. 12 is a detail of another embodiment of a drain, similar to the drain shown in FIG. 11, for a disposable fluid control island.

FIG. 12 shows a detail of another type of fitting, a bulkhead feed-through 66 fitted through the transition 60 for draining the fluid-containing vessel 48. The drain hose 64 connects to the hose barb 68 that extends from the transition 60.

Figure 13:
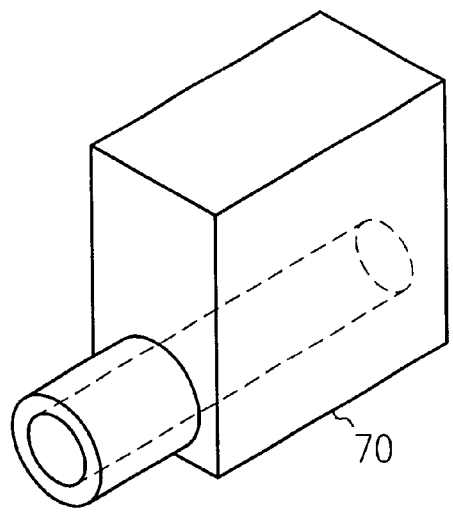
FIG. 13 is a detail of an optional embodiment of a drain tubing connector manifold adaptor.

FIG. 13 shows a transition manifold adaptor 70 that can be installed in place of a bulkhead feed-through 66 for convenient connection of a manifold 72.

Figure 14:
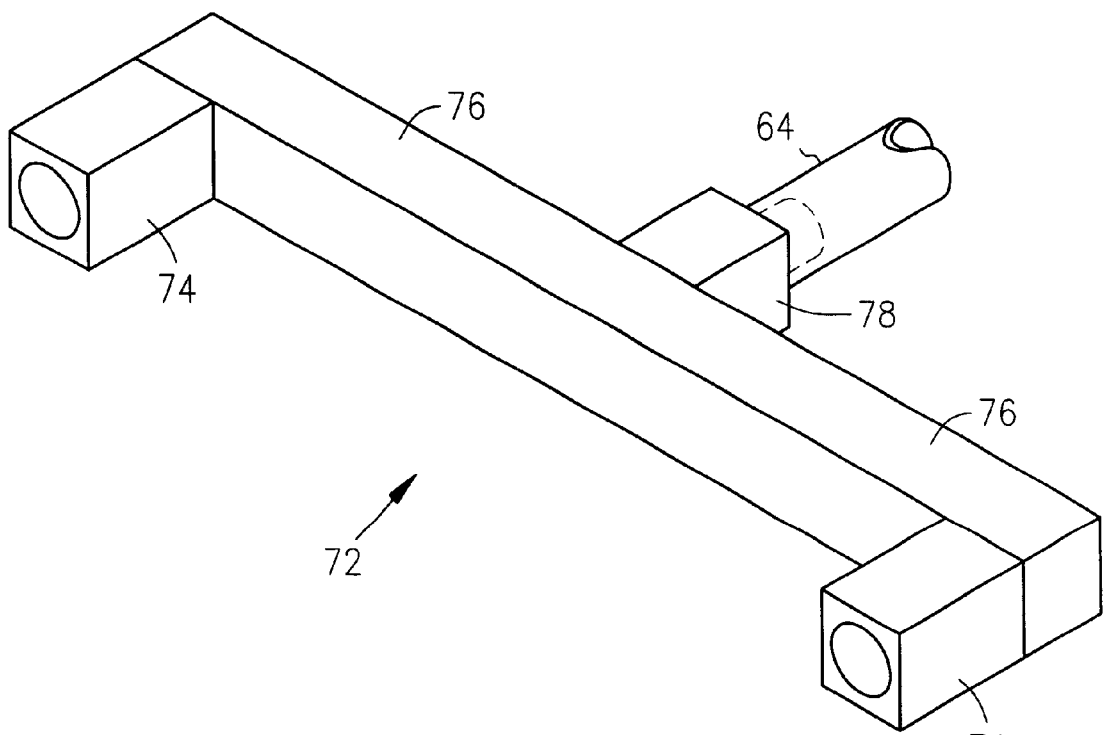
FIG. 14 is a detail of an exemplary drain manifold for a multiple section fluid control island of the type shown in FIG. 8.

FIG. 14 shows a manifold 72 that combines the fluids collected in more than one fluid control island module 22 so that the fluids may be collected and stored by a single drainage system 26. The manifold inlet 74 connects to a manifold adaptor 70 or to a drain hose 64. A hose barb 68 can be provided with, or fitted to, the manifold inlet 74. The fluids are drawn through the multiple manifold inlets 74 into a header 76. The header 76 may be designed to accommodate many manifold inlets 74, or may be designed to have only two inlets 74, as illustrated. A manifold outlet 78 transfers the fluids from the header 76 to a hose 64.

It is possible to form the header 76, inlets 74 and outlet integrally with the transition 30 or the alternate transition 60. As shown in FIG. 11, an integral header 79 may be formed to link a multiplicity of molded-in feed-throughs 62 to a single drain hose 64.

Referring again to FIG. 1, it may be seen that the drain hose 64 from the manifold outlet 78 leads to a collection tank 80. The drain system 26 shown collects fluids in a sealed collection tank 80 by drawing fluids through the drain hose 64 by vacuum. A pump 82 may be electrically operated or may be situated remotely and connected pneumatically to the collection vessel 80 by a vacuum hose 84. It may also be possible to locate a pressure pump 82 upstream from the collection tank 80 in some situations, but it is believed that vacuum operation will be used more frequently.

Changes and modifications in the specifically described embodiments can be carried out without departing from the scope of the invention which is intended to be limited only by the scope of the appended claims.

IDENTIFICATION OF DRAWING REFERENCE NUMBERS

| IDENTIFICATION OF DRAWING REFERENCE NUMBERS | |
| --- | --- |
| 20 | disposable fluid control island |
| 22 | fluid control island module |
| 24 | foot-supporting surface |
| 26 | drain system (overall) |
| 28 | vessel |
| 30 | transition |
| 32 | channel |
| 34 | channel lip |
| 36 | wall |
| 38 | latch |
| 40 | latch lip |
| 42 | latch wall |
| 44 | latch perimeter wall |
| 46 | transition inner wall |
| 48 | fluid-containing vessel |
| 50 | vessel latch wall |
| 52 | vessel channel wall |
| 54 | foot-supporting material |
| 56 | drain grooves |
| 60 | alternate transition |
| 62 | feed-through |
| 64 | drain hose |
| 66 | bulkhead feed-through |
| 68 | hose barb |
| 70 | manifold adaptor |
| 72 | manifold |
| 74 | inlet |
| 76 | header |
| 78 | outlet |
| 79 | integral header |
| 80 | collection tank |
| 82 | pump |
| 84 | vacuum hose |

What is claimed is:

1. A disposable fluid control island for selectably collecting, retaining and draining fluids from the vicinity of the feet of workers, comprising:
   a. a generally broad, shallow, impermeable vessel having a generally horizontal, floor contacting, bottom portion and a generally vertical peripheral portion;
   b. a foot supporting formed of a filler material comprised of hydrophobic, non-woven polymer fiber mesh, the filler having substantial liquid-receiving void space incorporated therein, the foot supporting portion disposed within and substantially filling the vessel while facilitating substantially free flow of liquid through void space of the filler material.

2. The apparatus defined in claim 1 further comprising a drain portion extending through the vessel, the drain portion being further comprised of a tubular portion communicating between the vessel and a disposal.

3. The apparatus defined in claim 1 wherein an inclined transition portion extends between the floor and the top surface of the foot-supporting portion.

4. The apparatus defined in claim 2 wherein an inclined transition portion extends between the floor and the top surface of the foot-supporting portion.

5. The apparatus defined in claim 4 wherein the bottom portion is inclined toward the drain portion.

6. The apparatus defined in claim 4 wherein the drain portion is further comprised of a multiplicity of fluid-conducting tubes, the tubes being hydraulically interconnected to a common conduit through which fluid is removed by a pump.

7. A method for supporting the feet of workers above spilled liquid, comprising:
   a. placing a generally broad, shallow, impermeable vessel having a generally horizontal, floor contacting bottom portion and a generally vertical peripheral wall portion on the floor of the work area,
   b. placing a foot-supporting portion formed of fluid permeable non-absorptive material substantially filling the vessel while facilitating a substantially free flow of fluid within the vessel,
   c. retaining fluid that falls in the vicinity of the workers feet in the vessel, and
   d. supporting the feet of the workers on the foot-supporting portion as fluid accumulates in the vessel.

8. The method defined in claim 7 further comprising the step of draining collected fluid from the vessel.

9. The method of claim 8 wherein the step of draining fluid from the vessel is performed using a pump.

10. The method of claim 9 further comprising the step of placing an inclined transition portion between the floor and the vessel.

11. The method of claim 7 further comprising the step of placing an inclined transition portion between the floor and the vessel.

12. The method defined in claim 11 further comprising the step of draining collected liquid from the vessel.

13. The method of claim 12 wherein the step of draining liquid from the vessel is performed using a pump.

14. A method for making a disposable fluid control island for selectably collecting, retaining and draining fluids from the vicinity of the feet of workers comprising the steps of:
   a. forming a generally broad, shallow, impermeable vessel,
   b. forming a foot-supporting portion of non-absorptive filler material, the filler material having a substantial liquid receiving void space therein, the foot supporting bottom portion filler material disposed within and substantially filling the vessel while facilitating a substantially free flow of fluid through the void space within the vessel.

15. The method defined in claim 14 further comprising the step of making a drain portion comprised of tubular material that extends through the vessel.

16. The method defined in claim 15 further comprising the step of fitting an inclined transition portion between the floor and the periphery of the top surface of the foot-supporting portion.

17. The method defined in claim 15 further comprising the step of inclining the bottom of the vessel toward the drain portion.

18. The method defined in claim 16 further comprising the step of inclining the bottom of the vessel toward the drain portion.

19. A disposable fluid control island for selectably collecting, retaining and draining fluids from the vicinity of the feet of workers, comprising:
   a. a generally broad, shallow, impermeable vessel having a generally horizontal, floor contacting, bottom portion and a generally vertical peripheral portion;
   b. a foot supporting portion with a bottom surface and a top surface spaced apart from the bottom surface by filler, the filler constructed of non-absorptive material having substantial fluid-receiving void space, the foot supporting portion disposed within and substantially filling the vessel,
   c. a drain portion operatively coupled to drain fluid passing through the void space of non-absorptive material of the foot-supporting portion, the drain portion being further comprised of a tubular portion communicating between the vessel and a disposal,
   d. an inclined transition portion disposed in communicating relationship between the floor and the top surface of the foot-supporting portion.

20. The apparatus defined in claim 19 wherein the bottom portion is inclined toward the drain portion.

21. The apparatus defined in claim 20 wherein the drain portion is further comprised of a multiplicity of fluid-conducting tubes, the tubes being hydraulically interconnected to a common conduit through which fluid is removed by a pump.

22. The apparatus defined in claim 19 wherein the filler is comprised of a non-woven polymer mesh.

23. The apparatus defined in claim 20 wherein the filler is comprised of a non-woven polymer mesh.

24. The apparatus defined in claim 21 wherein the filler is comprised of a non-woven polymer mesh.

25. The apparatus defined in claim 19 wherein the filler is comprised of a non-woven polymer mesh.

26. The apparatus defined in claim 20 wherein the filler is comprised of a non-woven polymer mesh.

27. The apparatus defined in claim 21 wherein the filler is comprised of a non-woven polymer mesh.

* * * * *

UNITED STATES PATENT AND TRADEMARK OFFICE
CERTIFICATE OF CORRECTION

PATENT NO.     : 6,568,419 B1
DATED          : May 27, 2003
INVENTOR(S)    : Allan R. Robinson and Dennis Ristvedt It is certified that error appears in the above-identified patent and that said Letters Patent is hereby corrected as shown below:

Column 8,
Line 43, after "peripheral" insert -- wall --.
Line 44, before "foot" insert -- unitary --.
Line 44, after "supporting" insert -- portion --.
Line 44, after "formed" insert -- substantially entirely --.
Line 48, after "vessel" delete "while" and insert therefor -- , a top surface thereof providing a traction surface for the feet of workers and providing a non-slip surface by --.
Line 49, after "through" insert -- the --.
Lines 64-65, delete "fluid-conducting" and insert therefor -- fluid conducting --.

Column 9,
Line 7, after "a" insert -- unitary --.
Line 7, after "formed" insert -- substantially entirely --.
Line 9, after "while" insert -- providing a traction and non-slip surface for the feet of workers by --.
Line 10, after "fluid" delete "within" and insert therefor -- from the surface of the foot-supporting portion into --.
Line 14, after "workers" insert -- directly --.
Line 33, delete "forming" and insert therefor -- providing --.
Line 35, delete "forming a" and insert therefor -- providing a unitary --.
Line 35, after "portion" insert therefor -- that is substantially entirely formed --.
Line 39, after "vessel" delete "while" and insert therefor --, top surface thereof providing a traction surface for the feet of workers and providing a non-slip surface by --.

Column 10,
Line 13, after "peripheral" insert -- wall --.
Line 15, delete "filler" and insert therefor -- a non-absorptive filler material that provides a traction and non-slip surface for the feet of workers, --.

UNITED STATES PATENT AND TRADEMARK OFFICE
CERTIFICATE OF CORRECTION

PATENT NO.   : 6,568,419 B1
DATED        : May 27, 2003
INVENTOR(S)  : Allan R. Robinson and Dennis Ristvedt It is certified that error appears in the above-identified patent and that said Letters Patent is hereby corrected as shown below:

<u>Column 10 contd,</u>
Line 15, before "material" delete "constructed of non-absorptive".
Line 16, after "space" insert -- that allows a substantially free flow of liquid therethrough --.

Signed and Sealed this

Twenty-ninth Day of June, 2004

JON W. DUDAS
*Acting Director of the United States Patent and Trademark Office*